US009648877B2

(12) United States Patent
Kupatt

(10) Patent No.: US 9,648,877 B2
(45) Date of Patent: *May 16, 2017

(54) METHODS FOR INCREASING TOLERANCE TO ABIOTIC STRESS IN PLANTS

(71) Applicant: Crop Microclimate Management Inc., Apex, NC (US)

(72) Inventor: Charles Christian Kupatt, Apex, NC (US)

(73) Assignee: Crop Microclimate Management Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/467,911

(22) Filed: Aug. 25, 2014

(65) Prior Publication Data

US 2014/0364314 A1    Dec. 11, 2014

Related U.S. Application Data

(63) Continuation of application No. 13/069,542, filed on Mar. 23, 2011, now Pat. No. 8,846,573.

(60) Provisional application No. 61/316,566, filed on Mar. 23, 2010.

(51) Int. Cl.
*A01G 7/06* (2006.01)
*A01N 37/04* (2006.01)
*A01N 37/10* (2006.01)

(52) U.S. Cl.
CPC .............. *A01N 37/10* (2013.01); *A01G 7/06* (2013.01); *A01N 37/04* (2013.01)

(58) Field of Classification Search
CPC ........... A01N 37/04; A01N 37/10; A01G 7/06
See application file for complete search history.

(56) References Cited

U.S. PATENT DOCUMENTS

| | | | |
|---|---|---|---|
| 2,603,560 A | 7/1952 | Stewart | |
| 3,897,241 A | 7/1975 | Washio et al. | |
| 6,710,018 B2 | 3/2004 | Smiley | |
| 6,987,130 B1 | 1/2006 | Yokoyama et al. | |
| 2004/0175722 A1 | 9/2004 | Kmiec et al. | |
| 2007/0149401 A1 | 6/2007 | Haskell et al. | |
| 2008/0274888 A1 | 11/2008 | Goldstein | |
| 2009/0048312 A1* | 2/2009 | Greenberg | A01N 37/04 514/367 |
| 2009/0156404 A1 | 6/2009 | Kupatt | |
| 2010/0048397 A1* | 2/2010 | Lewis | A01N 37/44 504/127 |

FOREIGN PATENT DOCUMENTS

| | | | |
|---|---|---|---|
| CL | 200603674 | 12/2006 | |
| IL | EP 0583774 A1 * | 2/1994 | A01N 65/00 |
| JP | 10-067610 A | 3/1998 | |
| JP | 2753635 B2 | 5/1998 | |
| SU | 115343 A | 11/1958 | |
| SU | 510462 A | 6/1976 | |
| WO | WO 2008020872 | 2/2008 | |

OTHER PUBLICATIONS

R. W. Marsh, "The use of copper sebacate as a foliage spray", Report—Long Ashton Research Station, 1943, 77-80, Abstract only.*
Agrios, George N., "Bacterial Cankers", *Plant Pathology* 2nd Edition, 1978, pp. 493-495.
Aleksieva, V. S. and Karanov, E. N., "Growth-retardant activity of certain aliphatic dicarboxylic acids and their diethyl esters", Doklady Bolgarskoi Akademii Nauk (1987), 40(1), 85-8.
D. Michael Glenn, Ernesto Prado, Amnon Erez, James McFerson and Gary J. Puterka, "A Reflective, Processed-Kaolin Particle Film Affects Fruit Temperature, Radiation Reflection, and Solar Injury in Apple", Journal of American Society of Horticultural Science, 127(2): 188-193, 2002.
D. S. Letham, "Regulators of Cell Division in Plant Tissues VI. The effects of Zeatin and Other Stimulants of Cell Division on Apple Fruit Development", New Zealand Journal of Agricultural Research, 1969, 12:1-20.
Hatfield et al., "Climate Impacts on Agriculture: Implications for Crop Protection," *Agronomy Journal*, vol. 103, Issue 2, 2011, pp. 351-370.
International Search Report and Written Opinion of International Application No. PCT/US2011/29556, mailed Jun. 1, 2011 (9 pages).
James English, Jr., James Bonner and A. J. Haagen-Smit, "The Wound Hormones of Plants. IV. Structure and Synthesis of a Traumatin", Journal of the American Chemical Society, 1939, 61(12), 3434-3436.
Jung et al., "Priming in Systemic Plant Immunity," *Science*, vol. 324, Apr. 3, 2009, pp. 89-91.
Manske et al., "Plant Water Stress Frequency and Periodicity in Western North Dakota," North Dakota State University, Dickinson Research Extension Center, 2006, 11 pages.
Manske et al., "Plant Water Stress Frequency" NDSU Dickinson Research Extension Center, Rangeland Research Extension Program Poster #6, 2006, 1 page.
Notification of Transmittal of International Preliminary Report on Patentability in corresponding International Application No. PCT/US2011/29556, mailed Apr. 26, 2012 (6 pages).
Spiers, Dr. A.G., "Management of Pseudomonas syringae", *Omnia Nutriology*, 2010, 6 Pages.
Haruta et al, "Syntheses and Plant Growth Retardant Activities of Trimethyl-ammonium Compounds Containing a Terpenoid Moiety", *Agr. Biol. Chem.*, 38(1), 1974, pp. 141-148.
Knight et al., "Studies on plant growth-regulating substances", *Ann. Appl. Biol.* (1969), 63, pp. 211-223.
Mishra et al., "*Arabidopsis* plants grown in the field and climate chambers significantly differ in leaf morphology and photosystem components", *BMC Plant Biology*, 2012, 12:6, 18 pages.

(Continued)

*Primary Examiner* — John Pak
*Assistant Examiner* — Nathan W Schlientz
(74) *Attorney, Agent, or Firm* — Myers Bigel, P.A.

(57) ABSTRACT

The present invention provides a method for increasing tolerance to abiotic stress and/or reducing the consequence of abiotic stress in a plant or part thereof comprising contacting a plant or part thereof with a composition comprising an effective amount of dicarboxylic acid or derivative thereof.

13 Claims, No Drawings

(56) References Cited

OTHER PUBLICATIONS

Tavakkoli et al., "A comparison of hydroponic and soil-based screening methods to identify salt tolerance in the field in barley", *Journal of Experimental Botany*, vol. 63, No. 10, 2012, pp. 3853-3868.
Bazzaz, F.A. "Photosynthesis of *Ambrosia artemisiifolia* L. Plants Grown in Greenhouse and in the Field", *Amer. Midland Naturalist* 90(1): 186-190 (1973).
Ghandilyan et al. "A strong effect of growth medium and organ type on the identification of QTLs for phytate and mineral concentrations in three Arabidopsis thaliana RIL populations", *J. Exp. Bot.* 60(5): 1409-1425 (2009).
Extended European Search Report for corresponding European Application No. 11760114.6, dated Jan. 31, 2017, 10 pages.
R.S. Gallagher et al., "Phenolic and Short-Chained Aliphatic Organic Acid Constituents of Wild Oat (*Avena fatua* L.) Seeds", *Journal of Agricultural and Food Chemistry*, vol. 58, No. 1, Jan. 13, 2010, pp. 218-225.

\* cited by examiner

METHODS FOR INCREASING TOLERANCE TO ABIOTIC STRESS IN PLANTS

STATEMENT OF PRIORITY

This application is a continuation application of U.S. patent application Ser. No. 13/069,542, filed Mar. 23, 2011, which claims the benefit, under 35 U.S.C. §119 (e), of U.S. Provisional Application No. 61/316,566, filed Mar. 23, 2010, the entire contents of each of which are incorporated by reference herein.

FIELD OF THE INVENTION

The present invention relates to the field of plant response to abiotic stress and provides methods and compositions for increasing the tolerance to abiotic stress in plants.

BACKGROUND OF THE INVENTION

Abiotic stresses negatively impact the growth and development of plants and result in significant reductions in crop yield and quality. Abiotic stresses include excessive or insufficient light intensity, cold temperature resulting in freezing or chilling, warm or high temperature, drought, ozone, salinity, toxic metals, nutrient poor soils, and the like. Further, exposure to prolonged exposure to abiotic stresses results in a greater susceptibility to biotic stresses such as pathogens and pests. Mittler, R., *Trends Plant Sci.* 11:15-19 (2006).

Plants acclimate to particular stress conditions using responses that are specific for that stress. As an example, during drought conditions, a plant closes its stomata to reduce water loss. However, plants are often subjected to a combination of stresses. For example, drought conditions often are combined with excessive heat conditions. In contrast to response to drought, a plant's response to heat is to open stomata so that the leaves are cooled by transpiration. This conflict in response reduces a plants ability to naturally adjust to such stresses.

A number of methods for alleviating abiotic stress in plants have been developed and many are available commercially. Thus, for example, shade netting, mesh, or cloth can be used to alleviate excessive heat and light. The use of reflective fabric, such as metalized surface plastics, white plastics, and foil materials on the ground of an orchard or vineyard can result in an increase in fruit size and yield with a concomitant reduction in fruit sunburn damage resulting from exposure to abiotic stress. Fruit surface temperature can be reduced through the application of low volumes of water, which cools the fruit through evaporative cooling of the surrounding air. A further method for alleviating heat stress includes the use of reflective, particle film technology (PFT), such as the commercial products RAYNOX®, SUNSHIELD® and SURROUND®. Many of the available products and methods described above have serious shortcomings. As a consequence, additional methods and products are needed for alleviating the stress caused by abiotic factors.

The present invention overcomes previous shortcomings in the art by providing methods and compositions that increase the tolerance to abiotic stress in plants.

SUMMARY OF THE INVENTION

The present invention provides a method for increasing tolerance to abiotic stress in a plant or part thereof comprising: contacting a plant or plant part thereof with a composition comprising an effective amount of dicarboxylic acid or derivative thereof, thereby increasing tolerance to abiotic stress in the plant or part thereof as compared to a control.

Thus, the present invention provides a method for increasing tolerance to abiotic stress in a plant or part thereof comprising: contacting a plant or plant part thereof with a composition comprising an effective amount of compound having the formula HOOC—R—COOH or derivative thereof, where R is a C5 to C14 alkylene.

In other embodiments, a method is provided for increasing tolerance to abiotic stress in a plant or part thereof comprising: contacting a plant or plant part thereof with a composition comprising an effective amount of a compound selected from the group consisting of pimelic acid (heptanedioic acid), suberic acid (octanedioic acid), azelaic acid (nonanedioic acid), sebacic acid (decanedioic acid), dodecanedioic acid, brassylic acid (tridecanedioic acid), thapsic acid (hexadecanedioic acid), salts thereof, and combinations thereof.

A further aspect of the invention provides a method for reducing the consequences of abiotic stress in a plant or part thereof comprising: contacting a plant or plant part thereof with a composition comprising an effective amount of dicarboxylic acid or derivative thereof, thereby reducing the consequences of abiotic stress in the plant or part thereof as compared to a control.

Thus, the present invention provides a method for reducing the consequences of abiotic stress in a plant or part thereof comprising: contacting a plant or plant part thereof with a composition comprising an effective amount of compound having the formula HOOC—R—COOH or derivative thereof, where R is a C5 to C14 alkylene.

In other embodiments, a method is provided for reducing the consequences of abiotic stress in a plant or part thereof comprising: contacting a plant or plant part thereof with a composition comprising an effective amount of a compound selected from the group consisting of pimelic acid (heptanedioic acid), suberic acid (octanedioic acid), azelaic acid (nonanedioic acid), sebacic acid (decanedioic acid), dodecanedioic acid, brassylic acid (tridecanedioic acid), thapsic acid (hexadecanedioic acid), salts thereof, and combinations thereof.

These and other aspects of the invention will be set forth in more detail in the description of the invention that follows.

DETAILED DESCRIPTION OF THE INVENTION

The present invention will now be described with reference to representative embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

DEFINITIONS

As used herein, "a," "an" or "the" can mean one or more than one (e.g., one, two, three, four, five, six, seven, eight, nine, ten, eleven, twelve, thirteen, fourteen, fifteen, etc). For example, a plant can mean a plurality of plants and a stress can refer to one or more stresses and equivalents thereof known to those of skill in the art.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

"Alkylene" as used herein refers to a difunctional linear, or branched alkyl group, which may be substituted or unsubstituted, and saturated or unsaturated, having from 1 to about 20 carbon atoms, e.g., 1, 2, 3, 4, 5, 6, 7, 8, 9, 10, 11, 12, 13, 14, 15, 16, 17, 18, 19, or 20 carbon atoms. Exemplary alkylene groups include methylene ($-CH_2-$); ethylene ($-CH_2-CH_2-$); propylene ($-(CH_2)_3-$); butylene ($-(CH_2)_4-$); pentylene ($-(CH_2)_5-$); hexylene ($-(CH_2)_6-$) septylene ($-(CH_2)_7-$), octylene ($-(CH_2)_8-$), nonylene ($-(CH_2)_9-$), and decylene ($-(CH_2)_{10}-$), and the like. Thus, an alkylene group can have 1 carbon atom to 10 carbon atoms (e.g., 1, 2, 3, 4, 5, 6, 7, 8, 9, or 10), 5 carbon atoms to 14 carbon atoms (e.g., 5, 6, 7, 8, 9, 10, 11, 12, 13, or 14) and/or 6 carbon atoms to 20 (e.g., 6, 7, 8, 9, 10, 11, 12, 13, 14, 15, 16, 17, 18, 19, or 20) carbons, and the like. As discussed above, the alkylene group can be optionally substituted. As an example, the alkylene group can be optionally substituted with one or more "alkyl group substituents."

The term "abiotic stress" as used herein refers to outside, nonliving, factors which can cause harmful effects to plants. Thus, as used herein, abiotic stress includes, but is not limited to, cold temperature that results in freezing, chilling, heat or high temperatures, drought, high light intensity, low light intensity, salinity, ozone, and/or combinations thereof. Parameters for the abiotic stress factors are species specific and even variety specific and therefore vary widely according to the species/variety exposed to the abiotic stress. Thus, while one species may be severely impacted by a high temperature of 23° C., another species may not be impacted until at least 30° C., and the like. Temperatures above 30° C. result in dramatic reductions in the yields of most important crops. This is due to reductions in photosynthesis that begin at approximately 20-25° C., and the increased carbohydrate demands of crops growing at higher temperatures. The critical temperatures are not absolute, but vary depending upon such factors as the acclimatization of the crop to prevailing environmental conditions. In addition, because most crops are exposed to multiple abiotic stresses at one time, the interaction between the stresses affects the response of the plant. For example, damage from excess light occurs at lower light intensities as temperatures increase beyond the photosynthetic optimum. Water stressed plants are less able to cool overheated tissues due to reduced transpiration, further exacerbating the impact of excess (high) heat and/or excess (high) light intensity. Thus, the particular parameters for high/low temperature, light intensity, drought and the like, which impact crop productivity will vary with species, variety, degree of acclimatization and the exposure to a combination of environmental conditions.

"Reduce," "reduced," "reducing" or "reduction," (and other grammatical variations thereof) as used herein means diminished, a decrease in, or a diminution in, for example, plant size, as a response to abiotic stress.

"Increase, "increased, or "increasing" (and other grammatical variations thereof) as used herein means an enhancement or augmentation of, for example, number of fruit produced by a plant, as a response to alleviating abiotic stress to which the plant is exposed.

The present invention provides a method for increasing tolerance to abiotic stress in a plant or part thereof comprising: contacting a plant or part thereof with a composition comprising an effective amount of dicarboxylic acid or derivative thereof, thereby increasing the tolerance to abiotic stress of the plant or part thereof as compared to a control plant or part thereof exposed to the same abiotic stress but not contacted with the compositions of the present invention comprising dicarboxylic acid or derivative thereof. In other embodiments of the present invention, a method is provided for reducing the consequence of abiotic stress in a plant or part thereof comprising: contacting a plant or part thereof with a composition comprising an effective amount of dicarboxylic acid or derivative thereof, thereby reducing the consequence of the abiotic stress in a plant or part thereof as compared to a control.

An "increased tolerance to abiotic stress" as used herein refers to the ability of a plant or part thereof exposed to abiotic stress and contacted with the compositions comprising dicarboxylic acid or derivative thereof to withstand a given abiotic stress better than a control plant or part thereof (i.e., a plant or part thereof that has been exposed to the same abiotic stress but has not been contacted with the compositions of the present invention). Increased tolerance to abiotic stress can be measure using a variety of parameters including, but not limited to, the size and number of plants or parts thereof, and the like (e.g., number and size of fruits), the level or amount of cell division, the amount of floral abortion, the amount of sunburn damage, crop yield, and the like. Thus, in some embodiments of this invention, a plant or part thereof having been contacted with a composition of the present invention comprising a dicarboxylic acid or derivative thereof, and having increased tolerance to the abiotic stress, for example, would have reduced flower abortion as compared to a plant or part thereof exposed to the same stress but not having been contacted with said composition.

"A consequence of abiotic stress" as used herein refers to the effects, results or outcome of exposure of a plant or part thereof to one or more than one (e.g., one, two, three, four, five, etc) abiotic stress. Thus, a consequence of abiotic stress includes, but is not limited to, sunburn damage, flower abortion, fruit drop, a reduction in the number of plants or parts there of, a reduction in produce quality (e.g., fruit quality) measured as color, finish, and/or shape (e.g., reduced quality of produce due to appearance and texture), a reduction in the size of plants or parts thereof, a reduction in cell division, and the like. Thus, the consequences of abiotic stress are typically those consequences which negatively impact on crop yield and quality.

"Reducing the consequence of abiotic stress" as used herein refers to the ability of a plant or part thereof exposed to abiotic stress and contacted with the compositions comprising dicarboxylic acid or derivative thereof to withstand a given abiotic stress better than a control plant or part thereof (i.e., a plant or part thereof that has been exposed to the same abiotic stress but has not been contacted with the compositions of the present invention), thereby diminishing or reducing the consequence of abiotic stress in the plant or part thereof. The consequence of abiotic stress can be measured using a variety of parameters including, but not limited to, the size and number of plants or parts thereof, and the like (e.g., number and size of fruits), the level or amount of cell division, the amount of floral abortion, the amount of fruit drop, the amount of sunburn damage, and the like, and combinations thereof. Thus, reducing the consequence of abiotic stress as used herein can also mean maintaining the size and number of plants or parts thereof, and the like (e.g., number and size of fruits), the level or amount of cell division, the amount of floral abortion, the amount of fruit drop and/or the amount of sunburn damage and/or other quality parameters (e.g., fruit color, finish and/or shape) as observed in a control plant which has not been exposed to the abiotic stress.

Thus, in some embodiments of this invention, a method is provided for reducing the amount of flower abortion or fruit drop in a plant or part thereof exposed to abiotic stress comprising: contacting the plant or part thereof with a dicarboxylic acid or derivative thereof, thereby reducing flower abortion or fruit drop as compared to a control plant or part thereof exposed to the same stress but not having been contacted with said composition.

In other embodiments, the consequence of abiotic stress is sunburn damage. Thus, in some particular embodiments, a method is provided for reducing sunburn damage in a plant or part thereof comprising: contacting a plant or part thereof with a composition comprising an effective amount of dicarboxylic acid or derivative thereof, thereby reducing the amount of sunburn damage as compared to a control plant or part thereof exposed to the same stress but not having been contacted with said composition. Thus, in some aspects of the invention, the abiotic stress is high temperature and high light intensity and the consequence of this combination of abiotic stresses is sunburn damage.

In still other embodiments, the consequence of abiotic stress is reduced fruit size. Thus, in some embodiments, a method is provided for reducing the reduction in fruit size in a plant or part thereof comprising: contacting a plant or part thereof with a composition comprising an effective amount of dicarboxylic acid or derivative thereof, thereby reducing the reduction in fruit size as compared to a control plant or part thereof exposed to the same stress but not having been contacted with said composition.

In some embodiments, the dicarboxylic acid of the present invention is a compound having the formula HOOC—R—COOH, wherein R is C5 to C14 alkylene. Thus, in some embodiments, R is C5, C6, C7, C8, C9, C10, C11, C12, C13, or C14 alkylene. Accordingly, in some embodiments of the present invention, R is C7 alkylene. In other embodiments, R is C8 alkylene. In still other embodiments, R is C9 alkylene. In additional embodiments, R is C10 alkylene.

Thus, in some embodiments of this invention, the dicarboxylic acid can be pimelic acid (heptanedioic acid), suberic acid (octanedioic acid), azelaic acid (nonanedioic acid), sebacic acid (decanedioic acid), dodecanedioic acid, brassylic acid (tridecanedioic acid), thapsic acid (hexadecanedioic acid), derivatives thereof, or combinations thereof. Accordingly, in some embodiments, a method for increasing tolerance to abiotic stress and/or reducing the consequence of abiotic stress in a plant or part thereof is provided, the method comprising: contacting a plant or part thereof with a composition comprising an effective amount of a dicarboxylic acid, wherein dicarboxylic acid can be azeleic acid. In other embodiments, the dicarboxylic acid can be, for example, sebacic acid. In further embodiments, the dicarboxylic acid can be any combination of dicarboxylic acids or derivatives thereof.

As discussed above, in some embodiments of the invention, a method for increasing tolerance to abiotic stress and/or reducing the consequence of abiotic stress in a plant or part thereof is provided comprising contacting a plant or part thereof with a composition comprising an effective amount of a dicarboxylic acid derivative. A derivative of dicarboxylic acid includes any compound that is derived from a dicarboxylic acid of the invention. Thus, in some embodiments, a derivative is a salt or an ester of a dicarboxylic acid. Non-limiting examples of a dicarboxylic acid salt include mono-sodium dicarboxylate, di-sodium dicarboxylate, mono-potassium dicarboxylate, di-potassium dicarboxylate, and the like. Examples of esters of dicarboxylic acids of the present invention include, but are not limited to, dimethyl-dicarboxylate, diethyl-dicarboxylate, dipropyl-dicarboxylate, dihexyl-dicarboxylate, di-(t-butyl)-dicarboxylate and the like. Thus, in some particular embodiments of the present invention, non-limiting examples of dicarboxylic acid derivatives include mono-sodium azelate, mono-potassium azelate, mono-sodium pimelate, di-sodium sebacic acid, mono-potassium brassylate or di-potassium sebacic acid, dimethyldodecanedioic acid, diethylthapsic acid, dipropylazelate, dihexylsuberic acid, di-(t-butyl)pimelate, and the like.

In some embodiments, the compositions comprising a dicarboxylic acid, or derivative thereof, can comprise one or more (e.g., one, two, three, four, five, six, seven, eight, nine, ten, eleven, twelve, thirteen, fourteen, fifteen, etc) different dicarboxylic acids or derivatives thereof. Thus, in some embodiments, this invention also provides a method for increasing tolerance to, and/or reducing the consequences, of abiotic stress in a plant or part thereof, comprising contacting the plant or part thereof with a composition comprising one, two, three, four, five, six, seven, or more dicarboxylic acids and/or derivatives thereof. In some aspects of the invention, a plant or part thereof may be contacted with a one or more than one composition (e.g., one, two, three, four, five, six, seven, eight, nine, ten, eleven, twelve, thirteen, fourteen, fifteen, etc) comprising one or more than one (e.g., one, two, three, four, five, six, seven, eight, nine, ten, eleven, twelve, thirteen, fourteen, fifteen, etc) dicarboxylic acid and/or derivative thereof. When the plant or part thereof is contacted with more than one composition comprising dicarboxylic acid or a derivative thereof, the compositions can be contacted with the plant or part thereof simultaneously, consecutively and/or intermittently.

An "effective" amount as used herein is an amount of a compound or composition that is sufficient to achieve the intended effect, e.g., to increase tolerance to abiotic stress in a plant or part thereof and/or reduce the consequence of abiotic stress plant or part thereof. The effective amount will vary with type of plant or crop, age, general condition of the plant or crop, the severity of the stress, the duration of the stress, the nature of any concurrent applications, the agriculturally acceptable carrier used (e.g., the specific formulation being used), and like factors that are within the knowledge and expertise of those skilled in the art. As appropriate, an "effective amount" in any individual case can be determined by one of ordinary skill in the art by reference to the pertinent texts and literature and/or by using routine experimentation. As used herein, an effective amount can comprise one or more than one application or dose of the compositions comprising a dicarboxylic acid or derivative thereof so as to achieve the desired increase in tolerance to abiotic stress and/or the desired reduction in the consequence of abiotic stress.

In some embodiments of the invention, a method for increasing the tolerance to, and/or reducing the consequence of abiotic stress in a plant or part thereof is provided comprising contacting the plant or part thereof with a composition comprising an effective amount of a dicarboxylic acid or derivative thereof, wherein an effective amount a dicarboxylic acid or derivative thereof is from about $1\times10^{-2}$ M to about $1\times10^{-9}$ M. Thus, in some embodiments, an effective amount of a dicarboxylic acid or derivative thereof is from about $1\times10^{-2}$ M to about $1\times10^{-8}$ M, from about $1\times10^{-2}$ M to about $1\times10^{-5}$ M, from about $1\times10^{-3}$ M to about $1\times10^{-4}$ M, from about $1\times10^{-3}$ M to about $1\times10^{-5}$ M, from about $1\times10^{-3}$ M to about $1\times10^{-8}$ M or from about $1\times10^{-4}$ M to about $1\times10^{-8}$ M, and the like. In other embodiments, an effective amount of a dicarboxylic acid or derivative thereof is about $1\times10^{-2}$ M, $1\times10^{-3}$ M, $1\times10^{-4}$ M, $1\times10^{-5}$ M, $1\times10^{-6}$ M, $1\times10^{-8}$ M, $1\times10^{-9}$ M, and the like, or combinations thereof. In still other embodiments of the present invention, an effective amount of a dicarboxylic acid or derivative thereof is about $2\times10^{-4}$ M, $3\times10^{-4}$ M, $5\times10^{-4}$ M, $2\times10^{-5}$ M, $3\times10^{-5}$ M, $5\times10^{-5}$, $2\times10^{-6}$ M, $3\times10^{-6}$ M, $4\times10^{-6}$ M, $2\times10^{-7}$ M, $3\times10^{-7}$ M, $6\times10^{-7}$ M, $2\times10^{-8}$ M, $2\times10^{-9}$ M, and the like.

In other embodiments, an effective amount of a dicarboxylic acid or derivative thereof is between about 0.00001 gram to about 1000 grams active ingredient per hectare. Thus, in some embodiments, an effective amount of a dicarboxylic acid or derivative thereof is between about 0.0001 gram to about 750 grams, between about 0.001 gram to about 500 grams active ingredient per hectare, between about 0.005 gram to about 250 grams active ingredient per hectare, between about 0.01 gram to about 100 grams active ingredient per hectare, between about 0.5 gram to about 50 grams active ingredient per hectare or between about 1 gram to about 25 grams active ingredient per hectare. In some particular embodiments, an effective amount of a dicarboxylic acid or derivative thereof is 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, and the like, grams active ingredient per hectare.

In additional embodiments of the invention, the composition comprising the dicarboxylic acid can be a concentration of between 0.1% and 99.9% by weight of active components. In other embodiments, the concentration of the composition comprising the dicarboxylic acid can be between 1.0% and 99% by weight of active components, between 0.5% and 95% by weight of active components, between 5% and 80% by weight of active components, between 10% and 75% by weight of active components, and the like.

The frequency of applying or contacting the plant or part thereof with a composition comprising a dicarboxylic acid and/or derivatives thereof can be as frequent as necessary to impart the desired effect of increased tolerance to, and/or reduced consequences of, abiotic stress and/or reducing the consequence of abiotic stress. For example, the composition can be contacted with the plant or part thereof one, two, three, four, five, six, seven, or more times per day, one, two, three, four, five, six, seven, eight, nine, ten, or more times per week, one, two, three, four, five, six, seven, eight, nine, ten, or more times per month, and/or one, two, three, four, five, six, seven, eight, nine, ten, or more times per year, as necessary to achieve increased tolerance to abiotic stress. Thus, in some embodiments the composition comprising dicarboxylic acid is contacted with the plant or part thereof 1 to 10 times per season, 1 to 11 times per season, 1 to 12 times per season, 1 to 13 times per season, 1 to 14 times per season, 1 to 15 times per season, and the like. In some embodiments, number of days between applications of (i.e., contacting the plant or part thereof with) the dicarboxylic acid and/or derivatives thereof is 1 day to 100 days, 1 day to 95 days, 1 day to 90 days, 1 day to 85 days, 1 day to 80 days, 1 day to 75 days, 1 day to 70 days, 1 day to 65 days, 1 day to 60 days, 1 day to 55 days, 1 day to 50 days, 1 day to 45 days, 1 day to 40 days, and the like, and any combination thereof. In still other embodiments of the present invention, the number of days between applications of the dicarboxylic acid and/or derivatives thereof is 1 day, 4 days, 7 days, 10 days, 13 days, 15 days, 18 days, 20 days, 25, days, 28, days, 30 days, 32, days, 35 days, 38 days, 40 days, 45 days, and the like, and any combination thereof. Accordingly, as one of skill in the art would recognize, the amount and frequency of application or contacting of the compositions of this invention to a plant or part thereof will vary depending on the plant/crop type, the condition of the plant/crop, the abiotic stress or consequences thereof being alleviated and the like. As one of skill in the art would additionally recognize based on the description provided herein, a composition of this invention can be effective for increasing tolerance to abiotic stress and/or reducing the consequence of abiotic stress in a plant or part thereof regardless of whether the initial application of the composition of the present invention is applied to the plant prior to, during, and/or after the initiation of the abiotic stress(es).

As discussed above, abiotic stress includes, but is not limited to, cold temperature, freezing, chilling, heat or high temperature, drought, high light intensity, salinity, ozone, and/or combinations thereof. In some particular embodiments of the present invention, the abiotic stress is freezing. In other aspects of the invention, the abiotic stress is chilling. In still other aspects of the invention, the abiotic stress is high light intensity. In additional embodiments of the invention, the abiotic stress is high temperature. As one of skill in the art would recognize, at any one time, a plant may be exposed to one or more abiotic stresses. (Mittler, R., *Trends Plant Sci.* 11(1) (2006)). Thus, in some embodiments of the invention, the term abiotic stress refers to a combination of stresses. Such combinations of stresses include, but are not limited to, high light intensity and high temperature; high light intensity and drought; high light intensity and salinity; high temperature and salinity; drought and high temperature; high light intensity and cold temperature; high light intensity, high temperature, and drought; high light intensity, high temperature, and salinity; and the like. Thus, in some particular embodiments, the combination of abiotic stresses is high temperature and high light intensity. In other embodiments, the combination of abiotic stresses is high temperature, high light intensity and drought. In further embodiments, the combination of abiotic stresses is high temperature and drought. In still further embodiments, the combination of abiotic stresses is high light intensity and drought. In yet other embodiments, the combination of abiotic stresses is cold temperature or chilling and high light intensity.

A plant or part thereof exposed to high temperature, alone or in combination with high light intensity can develop sunburn. Sunburn damage is a significant problem in the fruit industry resulting in losses in the millions of dollars. Three types of sunburn on fruit have been identified in, for example, apple studies. The first type is a necrotic spot on the sun-exposed side of the fruit resulting from the thermal death of cells in the peel when the surface temperature of the fruit reaches about 126° F. High temperature alone is sufficient to induce this condition. The second type is called "sunburn browning" and results in a yellow, bronze, or brown spot on the sun-exposed side of the fruit. This type of damage occurs in apples at a fruit surface temperature from about 115° F. to 120° F. and requires the presence of sunlight. The threshold temperature required for sunburn browning is cultivar dependent. The third type of sunburn damage occurs on fruit that is suddenly exposed to full sunlight, for instance, after thinning of tree branches or shifting of a branch as fruit load increases. This type of sunburn requires light and relatively low ambient temperatures (e.g., about 65° F.) with fruit surface temperature of about 88° F. Heat stress can also induce or enhance several skin and/or fruit disorders, including lenticel marking (dark spots), sunburn scald, cracking/splitting, misshapen fruit, bitter pit (blotchiness), "Fuji stain," and watercore. Sunburned/heat stressed tissues can also serve as entrance points for fungi and other pathogens. (See, US 20090280985)

Thus, in some embodiments, the present invention provides methods of increasing tolerance to high temperature in a plant or part thereof comprising contacting the plant or part thereof with a composition comprising an effective amount of dicarboxylic acid or derivative thereof, thereby increasing the tolerance of the plant or part thereof to high temperature and reducing sunburn damage as compared to a control (i.e., a plant or part thereof exposed to the same abiotic stress (i.e., high temperatures) but which has not been contacted with the compositions of the present invention). In other embodiments, a method is provided for increasing tolerance to high temperature and high light intensity in a plant or part thereof comprising contacting the plant or part thereof with a composition comprising an effective amount of dicarboxylic acid or derivative thereof, thereby increasing tolerance to high temperature and high light intensity and reducing sunburn damage as compared to a control.

In other embodiments, a method is provided for increasing tolerance to high temperature, high light intensity and drought in a plant or part thereof comprising contacting the plant or part thereof with a composition comprising an effective amount of dicarboxylic acid or derivative thereof, thereby increasing tolerance in a plant or part thereof to high temperature, high light intensity and drought as compared to a control. In additional embodiments, a method is provided for increasing tolerance to high temperature and drought in a plant or part thereof comprising contacting the plant or part thereof with a composition comprising an effective amount of dicarboxylic acid or derivative thereof, thereby increasing the tolerance to high temperature and drought as compared to a control. In further embodiments of this invention, a method is provided for increasing tolerance to high light intensity and drought in a plant or part thereof comprising contacting the plant or part thereof with a composition comprising an effective amount of dicarboxylic acid or derivative thereof, thereby increasing the tolerance to high light intensity and drought as compared to a control. In still further embodiments, a method is provided for increasing tolerance to drought in a plant or part thereof comprising contacting the plant or part thereof with a composition comprising an effective amount of dicarboxylic acid or derivative thereof, thereby increasing the tolerance to drought as compared to a control.

Abiotic stress such as high temperature can result in crop losses due to flower-abortion or fruit drop. Thus, in some embodiments of the present invention, methods are provided for increasing tolerance to high temperature in a plant or part thereof comprising contacting the plant or part thereof with a composition comprising an effective amount of a dicarboxylic acid or derivative of, thereby increasing the tolerance of the plant or part thereof to high temperature and reducing floral abortion as compared to a control (i.e., a plant or part thereof which has been exposed to the same abiotic stress conditions but has not been contacted with the compositions of the present invention comprising dicarboxylic acid or derivatives thereof). In other embodiments of the present invention, methods are provided for increasing tolerance to high temperature in a plant or part thereof comprising contacting the plant or part thereof with a composition comprising an effective amount of a dicarboxylic acid or derivative of, thereby increasing the tolerance of the plant or part thereof to high temperature and reducing fruit drop as compared to a control.

Cell division and fruit size are affected by abiotic stress including high temperature, high light intensity and/or drought. Each of these abiotic stress factors, alone or in combination, can result in reduced cell division and reduced fruit size. Thus, in some embodiments, the present invention provides methods for increasing tolerance to high temperature and/or high light intensity and/or drought in a plant or part thereof comprising contacting the plant or part thereof with a composition comprising an effective amount of a dicarboxylic acid or derivative of, thereby increasing the tolerance of the plant or part thereof to high temperature and/or high light intensity and/or drought and maintaining cell division and fruit size as compared to a control. In some particular embodiments, the present invention provides methods for increasing tolerance to high temperature in a plant or part thereof comprising contacting the plant or part thereof with a composition comprising an effective amount of a dicarboxylic acid or derivative of, thereby increasing the tolerance of the plant or part thereof to high temperature and maintaining cell division and fruit size as compared to a control.

The number and size of plants or parts thereof, the quality of the plant or plant part thereof that is produced (e.g., fruit quality) are also affected by abiotic stress. Thus, depending on the abiotic stress that a plant is exposed to the plant or plant part thereof can be reduced in the size and/or the number of plants or parts thereof can be reduced, and/or the quality of the produced plant or part thereof can be reduced (e.g., fruit size and/or quality). Quality can be measured as color, finish, and/or shape (e.g., reduced quality of produce due to appearance and texture). Thus, in some embodiments, the present invention provides methods for increasing tolerance to abiotic stress in a plant or part thereof comprising contacting the plant or part thereof with a composition comprising an effective amount of a dicarboxylic acid or derivative of, thereby increasing the tolerance of the plant or part thereof to abiotic stress and maintaining the number and/or size of a plant or part thereof as compared to a control. In other embodiments, the present invention provides methods for increasing tolerance to abiotic stress in a plant or part thereof comprising contacting the plant or part thereof with a composition comprising an effective amount of a dicarboxylic acid or derivative of, thereby increasing the tolerance of the plant or part thereof to abiotic stress and maintaining the quality of a plant or part thereof of as compared to a control.

In some aspects of the invention, the compositions comprising dicarboxylic acid or derivatives thereof further comprise an agriculturally acceptable carrier. An agriculturally-acceptable carrier of the present invention can include natural or synthetic, organic or inorganic material which is combined with the active component to facilitate its application to the plant, or part thereof. An agriculturally-acceptable carrier includes, but is not limited to, inert components, dispersants, surfactants, adjuvants, tackifiers, stickers, binders, or combinations thereof, that can be used in agricultural formulations.

Agriculturally acceptable carriers can be solid or liquid and are well known to those of skill in the art. Solid carriers include, but are not limited to, silicas, silica gels, silicates, talc, kaolin, limestone, lime, chalk, bole, loess, clay, attapulgite clay, bentonite, acid clay, pyrophillite, talc, calcite, corn starch powder, dolomite, diatomaceous earth, calcium sulfate, magnesium sulfate, magnesium oxide, ground synthetic materials, resins, waxes, fertilizers such as ammonium sulfate, ammonium phosphate, ammonium nitrate and ureas, products of vegetable origin such as cereal meal, tree bark meal, wood meal and nutshell meal (e.g., walnut shell powder), cellulose powders and the like; and combinations thereof. Non-limiting examples of liquid carriers include water, alcohols, ketones, petroleum fractions, aromatic or paraffinic hydrocarbons, chlorinated hydrocarbons, liquefied gases and the like, and combinations thereof. Thus, liquid carriers can include, but are not limited to, xylene, methylnaphthalene and the like, isopropanol, ethylene glycol, cellosolve and the like, acetone, cyclohexanone, isophorone and the like, vegetable oils such as soybean oil, cottonseed oil, corn oil and the like, dimethyl sulfoxide, acetonitrile, and combinations thereof.

In some embodiments, an agriculturally acceptable carrier of the present invention comprises a surface active agent (surfactant), which can be an emulsifying, dispersing or wetting agent of ionic or nonionic type. Non-limiting examples of surface active agents suitable for use with the compositions of the present invention, include alkyl benzene and alkyl naphthalene sulfonates, alkyl and alkyl aryl sulfonates, alkyl amine oxides, alkyl and alkyl aryl phosphate esters, organosilicones, fluoro-organic wetting agents, alcohol ethoxylates, alkoxylated amines, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, block copolymers, polyoxyalkylene derivatives of alkylphenols (particularly isooctylphenol and nonylphenol) and polyoxyalkylene derivatives of the mono-higher fatty acid esters of hexitol anhydrides (e.g., sorbitan).

Non-ionic surface active agents useful with the compositions of this invention include, but are not limited to, polyglycol ether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols. Other non-limiting examples of suitable non-ionic surface active agents include the water-soluble, 20 to 200 ethylene glycol ether groups containing polyadducts of ethylene oxide and polypropylene glycol, ethylene diamino polypropylene glycol and alkyl polypropylene glycol with 1 to 10 carbon atoms in the alkyl moiety. Additional non-limiting examples of non-ionic surface active agents include nonylphenol polyethoxy ethanols, castor oil polyglycol ether, fatty acid esters of polyoxy ethylene sorbitan, such as polyoxy ethylene sorbitan trioleate, polyadducts of ethylene oxide and polypropylene, tributyl phenoxy polyethoxy ethanol, polyethylene glycol, octyl phenoxy polyethoxy ethanol, Tween serials such as polyoxyethylene sorbitan monolaurate, polyoxyethylene sorbitan monopalmitate, polyoxyethylene sorbitan monooleate, and the like.

Non-limiting examples of dispersants useful with the compositions of the present invention include methyl, cellulose, polyvinyl alcohol, sodium lignin sulfonates, calcium lignosulfonates, polymeric alkyl naphthalene sulfonates, sodium naphthalene sulfonate, polymethylene binaphthalene sulfonate, and neutralized polyoxyethylated derivatives or ring-substituted alkyl phenol phosphates. In additional embodiments of this invention, the compositions comprising dicarboxylic acid and/or derivatives thereof can further comprise stabilizers, such as magnesium aluminum silicate, xanthan gum and the like.

Accordingly, in some embodiments, the compositions comprising dicarboxylic acid and/or derivatives thereof can be mixed with one or more agriculturally acceptable carriers, solid or liquid, and prepared by various means, e.g., by homogeneously mixing, blending and/or grinding the composition(s) with suitable carriers using conventional formulation techniques.

The compositions of the present invention can be made in any formulation suitable for applying to or contacting with a plant or part thereof. Formulations suitable for contacting the compositions of the invention to a plant or part thereof include, but are not limited to, a spray, a suspension, a powder, a granule, a mist, an aerosol, a foam, paste, emulsions (e.g., in oil (vegetable or mineral), or water or oil/water), a capsule, and combinations thereof.

Powders and dusts can be prepared by mixing or jointly grinding the active compound or compounds with a solid carrier. Granules (e.g. coated granules, impregnated granules or homogeneous granules) can be prepared by binding the active component to a solid carrier, Solutions can be prepared by dissolving the active component in a liquid carrier, optionally including a surface active agent.

In particular aspects of the present invention, the compositions comprising the dicarboxylic acid or derivative thereof can be used in combination with additional active compounds. Thus, in some embodiments, the compositions of this invention comprising dicarboxylic acid or derivatives thereof, further comprise additional active compounds. In other embodiments, the additional active compounds can be provided in one or more than one composition that is separate from the compositions comprising the dicarboxylic acid or derivative thereof. When provided in one or more than one separate compositions, the additional compounds can be contacted with the plant or part thereof, before, concurrent with, and/or within a few hours, several hours, and/or 1, 2, 3, 4, 5, 6, 7, 8, 9, and/or 10 days before or after contacting a composition of this invention to a plant or part thereof. Additional active compounds that are useful in combination with the dicarboxylic acid compounds of this invention include, but are not limited to, fertilizers, plant nutrients and micronutrients, amino acids, plant hormones and hormone-like compounds, pesticides, fungicides, insecticides, nematicides, reflective materials, and the like.

Thus, in some embodiments, the plant hormones and hormone-like compounds that can be used with the present invention include, but are not limited to, auxins, cytokinins, abscisic acid, gibberellins, ethylene, salicylic acid, and the like, and combinations thereof. In other embodiments, the amino acids that can be used with the present invention include, but are not limited to, glycine betaine, aminobutyric acid, and the like. In particular aspects of the present invention, the compositions comprising dicarboxylic acid and/or derivatives thereof further comprise salicylic acid. In other aspects of the present invention, the compositions comprising dicarboxylic acid and/or derivatives thereof further comprise glycine betaine. In still other aspects, compositions comprising dicarboxylic acid and/or derivatives thereof further comprise salicylic acid and glycine betaine. In some additional embodiments of the present invention, the composition comprising dicarboxylic acid further comprises furanocoumarin, terpenes, tripenes, pinene, 2-carene, phellandrene, rosmarinic acid, benzyl acetate, and the like.

In other embodiments, the compositions comprising dicarboxylic acid and/or derivatives thereof further comprise kaolin and/or calcium carbonate, and/or combinations thereof. Thus, in some embodiments of this invention, the compositions comprising dicarboxylic acid further comprise kaolin. In other embodiments, the compositions of the present invention further comprise calcium carbonate. In still further embodiments, the compositions of the present invention comprising dicarboxylic acid and derivatives thereof, further comprise kaolin and calcium carbonate.

In some embodiments, the compositions comprising dicarboxylic acid and/or derivatives thereof that further comprise additional active components can comprise an amount of each additional active ingredient between about 0.00001 gram to about 1000 grams active ingredient per hectare. Thus, in some embodiments, the amount of each additional active ingredient can be between about 0.0001 gram to about 750 grams, between about 0.001 gram to about 500 grams active ingredient per hectare, between about 0.005 gram to about 250 grams active ingredient per hectare, between about 0.01 gram to about 100 grams active ingredient per hectare, between about 0.5 gram to about 50 grams active ingredient per hectare or between about 1 gram to about 25 grams active ingredient per hectare. In some particular embodiments, the amount of each additional active ingredient can be 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, and the like, grams active ingredient per hectare.

In some embodiments, the compositions comprising dicarboxylic acid and/or derivatives thereof that further comprise kaolin, can comprise an amount of kaolin in a range of about 5 kg/ha to about 100 kg/ha. Thus, in some embodiments, the amount of kaolin can be in a range of about 5 kg/ha to about 100 kg/ha, about 5 kg/ha to about 10 kg/ha, about 5 kg/ha to about 15 kg/ha, about 5 kg/ha to about 20 kg/ha, about 5 kg/ha to about 30 kg/ha, about 5 kg/ha to about 40 kg/ha, about 5 kg/ha to about 50 kg/ha, about 5 kg/ha to about 60 kg/ha, about 5 kg/ha to about 70 kg/ha, about 5 kg/ha to about 80 kg/ha, about 5 kg/ha to about 90 kg/ha, about 15 kg/ha to about 30 kg/ha, about 15 kg/ha to about 40 kg/ha, about 15 kg/ha to about 50 kg/ha, about 15 kg/ha to about 60 kg/ha, about 15 kg/ha to about 80 kg/ha, about 15 kg/ha to about 90 kg/ha, about 15 kg/ha to about 100 kg/ha, about 20 kg/ha to about 50 kg/ha, about 20 kg/ha to about 80 kg/ha, about 20 kg/ha to about 100 kg/ha, about 40 kg/ha to about 80 kg/ha, about 40 kg/ha to about 100 kg/ha, about 50 kg/ha to about 80 kg/ha, about 50 kg/ha to about 100 kg/ha, about 75 kg/ha to about 100 kg/ha, and the like.

As discussed above, the dicarboxylic acid compositions can be contacted with a plant or part thereof with other compounds that are included the same composition/formulation or in separate compositions/formulations. Thus, the kaolin and/or calcium carbonate, and the like, or combinations thereof, can be in the same composition/formulation with the dicarboxylic acid compositions of this invention or can be provided in one or more than one (e.g., one, two, three, four, five, six, seven, eight, nine, ten, eleven, twelve, thirteen, fourteen, fifteen, etc) separate compositions/formulations. When provided in separate compositions/formulations, the plant and part thereof can be contacted with the dicarboxylic acid composition before, concurrent with, or after, the plant or part thereof is contacted with the reflective compounds.

In further aspects of the invention, the plant or part thereof can be contacted with the compositions of the present invention comprising dicarboxylic acid, wherein the compositions can further comprise any combination of other useful compounds including, but not limited to, those discussed above. Thus, the compositions comprising dicarboxylic acid can further comprise additional useful compounds including, but not limited to, kaolin, calcium carbonate, salicylic acid, glycine betaine, and the like, in any combination. Thus, for example, the compositions comprising dicarboxylic acid can further comprise kaolin and salicylate.

In other embodiments, the plant or part thereof contacted with compositions of the present invention comprising dicarboxylic acid or derivative thereof are further contacted with one or more than one useful compound present in one or more than one composition separate from the composition(s) comprising dicarboxylic acid or derivative thereof. As discussed above, the order of application of the compositions can vary according to need.

In some aspects of the invention, the step of contacting the plant or part thereof includes any method by which the compositions of the invention are brought into contact with the plant or part thereof. The term "contact" comprises any method in which a plant is exposed to, provided with, or in which a compound is applied to a plant or part thereof. Some non-limiting examples of contacting a plant or part thereof include spraying, dusting, sprinkling, scattering, misting, atomizing, broadcasting, soaking, soil injection, soil incorporation, drenching (e.g., soil treatment), pouring, coating, leaf or stem infiltration, side dressing or seed treatment, and the like, and combinations thereof. These and other procedures for contacting a plant or part thereof with compound(s), composition(s) or formulation(s) are well-known to those of skill in the art.

As used herein, the surface of the plant and part thereof includes the plant and parts thereof that are above and below the ground. In some particular embodiments of this invention, the composition is contacted with/applied to the surface of the plant or plant part, which composition is then absorbed into the plant.

Thus, a plant or part thereof of the present invention includes, but is not limited to, the whole plant, the above and below ground parts of the plant, leaves, needles, stems, buds, flowers and parts thereof, fruits and parts thereof, cones and parts thereof, stems, seeds, roots, tubers, rhizomes, and combinations thereof. A whole plant includes all stages of development from seed and seedling to mature plant. Thus, in some embodiments of the invention, the plant is a seed. In other embodiments of the invention, the plant is a seedling. In still other embodiments, the plant is mature and can bear flowers and fruit (i.e., sexually reproduce). A plant may be contacted with the compositions of the present invention at all stages of plant development. As would be well understood in the art, the stage or stages of development during which the compositions of the present invention would be contacted with compositions of the present invention would depend upon the species of plant, the plant part and the stress to which the plant or part thereof is exposed. In some particular aspects of the invention, the stage of development at which a plant is contacted with the compositions of the invention is at petal fall.

The methods of the present invention are useful for any type of plant or part thereof exposed to or which may become exposed to an abiotic stress. Thus, plants useful for the present invention include, but are not limited to, gymnosperms, angiosperms (monocots and dicots), ferns, fern allies, bryophytes, and combinations thereof.

Specific non-limiting examples of a plant or part thereof of the present invention include woody, herbaceous, horticultural, agricultural, forestry, nursery, ornamental plant species and plant species useful in the production of biofuels, and combinations thereof. In other embodiments, the plant or part thereof includes, but is not limited to, apple, tomato, pear, pepper (Capsicum), bean (e.g., green and dried), cucurbits (e.g., squash, cucumber, honeydew melon, watermelon, cantaloupe, and the like), papaya, mango, pineapple, avocado, stone fruits (e.g., plum, cherry, peach, apricot, nectarine, and the like), grape (wine and table), strawberry, raspberry, blueberry, mango, cranberry, gooseberry, banana, fig, citrus (e.g., clementine, kumquat, orange, grapefruit, tangerine, mandarin, lemon, lime, and the like), nuts (e.g., hazelnut, pistachio, walnut, macadamia, almond, pecan, and the like), lychee (Litchi), soybeans, corn, sugar cane, peanuts, cotton, canola, oilseed rape, sunflower, rapeseed, alfalfa, timothy, tobacco, tomato, sugarbeet, potato, pea, carrot, cereals (e.g., wheat, rice, barley, rye, millet, sorghum, oat, triticale, and the like), buckwheat, quinoa, turf, lettuce, roses, tulips, violets, basil, oil palm, elm, ash, oak, maple, fir, spruce, cedar, pine, birch, cypress, coffee, miscanthus, arundo, switchgrass, and combinations thereof.

Thus, in some embodiments of the present invention, the plant or part thereof is a tomato. In other embodiments, the plant or part thereof is a citrus tree. In still other embodiments, the plant or part thereof is an apple tree. In further embodiments, the plant or part thereof is a stonefruit. In still further embodiments, the plant or part thereof is a wine grape plant.

Other aspects of the invention comprise the use of a compound or composition of the present invention for carrying out the methods of the present invention described herein.

The following examples are included to demonstrate various embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1

Field Trials

Field trials were carried out in parts of commercial orchards or fields in Australia during the 2009-2010 season. Crops were evaluated for specific parameters impacted by abiotic stress including fruit diameter, fruit number, amount of sunburn damage and number of flowers aborted. The crops evaluated were apple, citrus, tomato and wine grape. The crops in the trials received normal fungicide applications and were observed to be disease free. Heat and light stress occurred early during the trials, with exposures to 40° C.+ temperatures in November; about 4-6 weeks after the trials were initiated. This period of stress was followed by varied temperatures including temperatures that were in the mid-to-high 30° C. range.

Treatments included (1) None; (2) Screen; (3) Screen Duo; (4) azelaic acid; (5) Screen+azelaic acid (CMM2009A=the code for azeleic acid used during trials); (6) Screen Duo+azeleic acid; (7) azeleic acid+salicylic acid; (8) azeleic acid+glycine betaine; (7) Surround; and (8) Parasol, The foliage and fruit for each crop were assessed prior to treatment and then at regular intervals through the season for any signs of phytotoxicity. No phytotoxicity was observed on either the foliage or the fruit for any of the applied formulations for any of the crops. In addition, all trials were determined to be disease and pest free.

The treatments and rates at which the treatments were applied to the plants or parts thereof are provided in Table 1, below. Screen (kaolin), Screen Duo (kaolin and salicylate), Surround (kaolin) and Parasol (calcium carbonate) are standard treatments used in the management of heat, light and water stress. Kaolin and calcium carbonate reduce stress by reflecting UV, visible, and infrared radiation, thereby reducing the impact of excess heat and light on photosynthesis and other cellular processes.

The citrus and apple trials received four and five applications, respectively, of the various formulations, set forth in Table 1 (below), prior to experiencing abiotic stress. Tomatoes received biweekly applications of the treatments throughout the trial.

The various stages of fruit development are (1) cell division; (2) pit hardening—in stone fruits only; (3) cell enlargement and (4) fruit maturation. The fruit of each crop described herein were in Stage I of fruit development (cell division phase) and thus, susceptible to damage due to high temperature as measured by reduced fruit size and number.

TABLE 1

Treatments and rates applied in the field trials (in parenthesis are the rates applied to tomatoes).

| Treatment | Rate - first treatment | Rate - second treatment |
| --- | --- | --- |
| Screen (kaolin) | 2.5 kg/100 L (25 kg/ha) | 1.25 kg/100 L (12.5 kg/ha) |
| Screen Duo (kaolin and salicylate) | 1.25 kg/100 L (12.5 kg/ha) | 0.625 kg/100 L (6.25 kg/ha) |
| Azelaic acid (CM2009A) | 8-18 g/ha | 8-18 g/ha |
| Screen and | 2.5 kg/100 L (25 kg/ha) | 1.25 kg/100 L (12.5 kg/ha) |
| Azelaic acid | 8-18 g/ha | 8-18 g/ha |
| Screen Duo and | 1.25 kg/100 L (12.5 kg/ha) | 0.625 kg/100 L (6.25 kg/ha) |
| Azelaic acid | 8-18 g/ha | 8-18 g/ha |
| Azelaic acid and | 8-18 g/ha | 8-18 g/ha |
| Salicylate | 1 g/L (10−4M) | 1 g/L (10−4M) |
| Azelaic acid and | 8-18 g/ha | 8-18 g/ha |

TABLE 1-continued

Treatments and rates applied in the field trials (in parenthesis are the rates applied to tomatoes).

| Treatment | Rate - first treatment | Rate - second treatment |
|---|---|---|
| Glycine betaine | 1 g/L (10-4M) | 1 g/L (10-4M) |
| Surround (kaolin) | 5 kg/100 L (50 kg/ha) | 2.5 kg/100 L (25 kg/ha) |
| Parasol (calcium carbonate) | 2 L/100 L | 1 L/100 L |

*the rate of water per hectare varied with the crop and therefore the rate of azelaic acid, azelaic acid and salicylate (CMM2009B = the code used for the combination during trials), azelaic acid and glycine betaine (CMM2009C = the code used for the combination during the trials) varied in g/ha applied.

Dicarboxylic acid treatments, alone or in combination with kaolin or various threeway were compared with standard treatments for management of heat, light and water stress including kaolin (Screen, Surround), kaolin+salicylate (Screen Duo), and calcium carbonate (Parasol). See Table 1, above. None of these treatments, with the exception of salicylate, have been reported to provide any significant degree of disease control. (Jung et al., *Science* 324:89-91 (2009); U.S. Patent Application No. 20090048312).

Example 2

Citrus Trial

In general, a lower fruit load results in greater fruit diameter at harvest. Early season differences in fruit diameter are due to variation in cell division. It is well documented that at equal fruit load, heat stress will result in smaller fruit (i.e., reduced fruit diameter). In addition, heat, light, and/or water stress can also result in fruit number losses, commonly known in citrus as "June drop." Past studies indicate that protecting the crop with Screen/Duo starting at petal fall can result in larger fruit and higher numbers of fruit, most likely by reducing the crop temperature and reducing stress signaling reactive oxygen (ROX).

The trial described below was conducted in Cobram, Victoria, Australia. Several parameters were measured as responses to heat, light and/or water stress: early citrus fruit diameter, number of fruit per cubic meter foliage, percent sunburn, later season fruit diameter and kilograms of fruit per cubic meter foliage. Sunburn damage is the late stage result of combined heat and light stress. Azelaic acid alone was as effective as the standard treatments (Screen, Screen Duo, Surround and Parasol) in protecting cell division, as measured by early fruit diameter. See Table 2, below. Azelaic acid was also as effective in reducing fruit loss; in fact, the highest numerical fruit loads were observed with the azelaic acid only treatments. In addition, adding azelaic acid to Screen also resulted in increased fruit diameter. The same was not observed for azelaic acid in combination with Screen Duo, which contains salicylate, or with the salicylate and azelaic acid combination, although there was no statistical separation between the azeleic acid and Screen Duo combination versus the salicylic acid and azeleic acid combination. There was little correlation observed between fruit number and fruit size (correlation coefficient=0.51). Finally, azelaic acid also provided protection from sunburn damage that was equal to that obtained using the standard treatments.

TABLE 2

Summary of the data from the citrus field trials

| Treatment | Rate* | 14-Dec-10 Fruit Diameter (mm) | 6-Jan-10 Fruit Number per cubic meter | 28-Jan-10 Percent Sunburn | 12-Apr-10 Fruit Diameter (mm) | 29-Sep-10 kgs/cubic meter of foliage |
|---|---|---|---|---|---|---|
| Untreated | | 27.52 | 5.34 | 13.6 | 66.68 | 2.3 |
| Screen | 2.5% fb** 1.25% | 29.14 | 9.26 | 6.3 | 71.37 | 3.3 |
| Screen Duo | 1.25% fb 0.65% | 29.51 | 8.90 | 3.0 | 71.25 | 3.5 |
| Azeleic acid (CMM2009A) | 18 g/ha | 29.49 | 10.62 | 5.6 | 71.59 | 3.8 |
| Screen + Azeleic acid | 2.5% + 18 g/ha fb 1.25% + 18 g/ha | 30.07 | 9.48 | 4.9 | 71.47 | 3.4 |
| Screen Duo + Azeleic acid | 1.25% + 8 g/L fb 0.65% + 8 g/L | 28.97 | 8.60 | 6.1 | 71.52 | 3.4 |
| Azeleic acid + Salicylate | 18 g/ha 1 g/L | 28.69 | 10.78 | 3.3 | 71.51 | 4.3 |
| Azeleic acid + Glycine Betaine | 18 g/ha 1 g/L | 29.20 | 8.46 | 4.8 | 71.28 | 3.3 |
| Surround | 5.0% fb 2.5% | 28.04 | 8.48 | 4.0 | 71.61 | 3.2 |
| Parasol | 2 fb 1 L/100 L | 29.77 | 8.34 | 5.9 | 69.77 | 2.7 |
| LSD 0.05 | | 1.38 | 2.58 | 3.1 | 0.48 | 0.3 |

*Four applications for all treatments.
**fb = followed by

Example 3

Apple Trial

As described above for citrus, early season heat, light and/or water stress can also impede cell division that occurs during Phase I of fruit development of apples. In the apple trial, which was conducted in Shepparton, Victoria, Australia, the load of fruit on each of the trees was thinned to an approximately equal value (approximately 200 fruit per tree; +/−5%), thus eliminating the confounding effect of fruit load on fruit diameter. To assess sunburn/heat stress damage, all apples were harvested from the center tree in each plot and rated according to the following rating system.

| Rating | Visual assessment of the fruit |
|---|---|
| 0 | No sunburn |
| 1 | Slight yellowing on the exposed side (<5% of the fruit area) |
| 2 | Noticeable yellowing on the exposed side (>5% of the fruit area) |
| 3 | Moderate sunburn with pronounced lenticels (fruit unmarketable) |
| 4 | Significant sunburn (fruit unmarketable) |

The data show that azelaic acid, alone or in combination with kaolin, salicylate, glycine betaine, or multiples thereof, was as effective as the standard treatments in protecting cell division as measured by fruit diameter, percent sunburn, apple size, yield and marketable yield. See Table 3, below.

Example 4

Tomato Trial

Flower abortion in tomato results in significant yield losses in tomato and begins at temperatures of 28 C, becoming more severe as temperatures rise. Further, once fruit has developed, it is susceptible to damage from heat and light, expressed as sunburn.

In the present study, tomatoes, located in a commercial field outside Echuca, Victoria, Australia, were treated with azeleic acid (CMM2009A). The number of aborted flowers per plot was assessed periodically during the season. Tomato yield and sunburn damage was assessed as follows. Tomatoes from the center of each plot were harvested from a one meter section of the tomato beds. The fruit was visually assessed as being either red in color and suitable for processing, green in color, or sun burnt. The fruit from these three categories were kept separate, weighed and recorded.

Treatment with azelaic acid was observed to reduce the number of flowers aborted to the same degree as the standard treatments for this type of abiotic stress. In addition, azelaic acid, applied alone or in combination with salicylate, kaolin, glycine betaine, or combinations thereof, provided protection from sunburn damage that was equivalent to or better than the standard treatments. See Table 4, below. No differences in foliage quality or crop vigor were observed between the treatments.

TABLE 3

Summary of the data from the apple field trials.

| Treatment | Rate* | 12-Dec-10 Fruit Diameter mm | 16-Feb-10 % Fruit Sunburn 1&2** | Apple Size g/apple | 17-Mar-10 Yield kg/tree | Marketable Yield kg/tree |
|---|---|---|---|---|---|---|
| Untreated | | 36.9 | 76.8 | 134 | 37 | 28.4 |
| Screen | 2.5% fb 1.25% | 40.37 | 89.9 | 154 | 44.8 | 40.3 |
| Screen Duo | 1.25% fb 0.65% | 39.81 | 89.8 | 152 | 45.4 | 40.8 |
| Azeleic acid (CMM2009A) | 18 g/ha | 39.84 | 87.4 | 152 | 42.8 | 37.4 |
| Screen + Azeleic acid | 2.5% + 18 g/ha fb 1.25% + 18 g/ha | 39.66 | 87.7 | 151 | 44.6 | 39.1 |
| Screen Duo + Azeleic acid | 1.25% + 18 gha fb 0.65% + 18 g/ha | 39.67 | 89 | 151 | 45.1 | 40.1 |
| Azeleic acid + Salicylate | 18 g/L 1 g/L | 39.52 | 88.2 | 156 | 45.5 | 40 |
| Azeleic acid + Glycine Betaine | 18 g/L 1 g/L | 40.52 | 90.5 | 160 | 45.5 | 41.2 |
| Surround | 5.0% fb 2.5% | 39.16 | 88.5 | 151 | 43.8 | 38.8 |
| Parasol | 2 fb 1 L/100 L | 41.16 | 89.9 | 154.5 | 45.9 | 41.2 |
| LSD 0.05 | | 1.62 | 2.68 | 9.53 | 3.9 | 3.59 |

*Four applications for all treatments

**1&2 are export grade apples, or commercially acceptable grade apples. Fruit that falls outside grades 1&2 are lower quality and are juiced.

TABLE 4

Summary of the data from the tomato field trials.

| Treatment | Rate* | 20-Jan-10 Aborted Flowers per sq m of the plot | 20-Feb-10 Number Sunburn Fruit per plot | 12-Mar-10 Yield Red MT/ha | 12-Mar-10 Yield Sunburn MT/ha | 12-Mar-10 Total Yield MT/ha | Soluble Solids MT/ha |
|---|---|---|---|---|---|---|---|
| Untreated | | 13.3 | 45 | 99.5 | 17.5 | 121.7 | 4.5 |
| Screen | 25 kg/ha fb 12.5 kg/ha | 2.8 | 23.3 | 145.6 | 9 | 154.6 | 6.6 |
| Screen Duo | 12.5 kg/ha fb 6.25 kg/ha | 3 | 23.5 | 134.6 | 10.4 | 145 | 6.2 |
| Azeleic acid (CMM2009A) | 8 g/ha | 5 | 21.3 | 131 | 6.6 | 137.6 | 6.2 |
| Screen + Azeleic acid | 25 kg + 8 g/ha fb 12.5 kg + 8 g/ha | 2 | 18 | 144.7 | 11.5 | 156.2 | 6.6 |
| Screen Duo + Azeleic acid | 12.5 kg + 8 g/ha fb 6.25 kg + 8 g/ha | 5 | 23.5 | 135.7 | 11 | 146.7 | 6.2 |
| Azeleic acid + Salicylate | 8 g/ha 1 g/L | 4.0 | 19.8 | 137.3 | 9 | 146.4 | 6.3 |
| Azeleic acid + Glycine Betaine | 8 g/ha 1 g/L | 2.5 | 14.0 | 140.1 | 10.7 | 150.8 | 6.4 |
| Surround | 50 kg/ha fb 25 kg/ha | 3 | 21.8 | 146.1 | 12.1 | 158.2 | 6.8 |
| Parasol | 6.25 L/ha | 3 | 21.8 | 120.6 | 12.6 | 133.2 | 5.5 |
| LSD 0.05 | | 2.37 | 9.38 | 10.64 | 3.48 | 10.9 | 0.5 |

*Ten applications for all treatments.

Example 5

Tomato Pot Trials

Tomato plants were exposed to heat and light stress in the greenhouse. Control plants had no treatment or were treated with Screen, Screen Plus1, Screen Plus2, or Screen Plus3, The experimental plants were treated with azeleic acid at $10^{-4}$M or $10^{-3}$M applied alone or in combination with Screen, Screen Plus1, Screen Plus2, or Screen Plus3. The results are set forth below in Table 5 and show that azelaic acid at $10^{-4}$M provided protection from the abiotic stress that was equivalent to or better than the standard treatments as measured by average fruit size.

TABLE 5

Average change in growth (cm) of tomato fruits exposed to heat and light stress in response to various treatments.

| Azelaic | Screen* | April 2-May 10 Avg. growth in cm. | April 2-May 18 Avg growth in cm. |
|---|---|---|---|
| None | None | 8.1 | 6.1 |
| None | Screen | 8.9 | 6.1 |
| None | Screen Plus1 | 11.5 | 9.0 |
| None | Screen Plus2 | 11.0 | 8.5 |
| None | Screen Plus3 | 10.7 | 7.9 |
| Azelaic $10^{-4}$M | None | 11.0 | 8.7 |
| Azelaic $10^{-4}$M | Screen | 10.1 | 8.5 |
| Azelaic $10^{-4}$M | Screen Plus1 | 10.5 | 7.7 |
| Azelaic $10^{-4}$M | Screen Plus2 | 10.7 | 7.4 |
| Azelaic $10^{-4}$M | Screen Plus3 | 9.6 | 7.9 |
| Azelaic $10^{-3}$M | None | 8.0 | 6.1 |

*All Screen applications were applied at a rate equivalent of 25 kg/ha.

Example 6

Wine Grape Trial

The trial described below was conducted in Kialla, Victoria, Australia. The trial design was a randomized complete block with four replicates. Each plot comprises one panel of vines having four vines. For yield measurements the grapes were harvested from each of the two center vines in each panel and bunch numbers and weights were recorded. For assessment of sunburn/heat stress damage, the bunches of grapes were rated according to the following system:

| Rating | Incidence of sunburn/heat stress on grape bunches (%) |
|---|---|
| 1 | 0 |
| 2 | 1-5 |
| 3 | 6-10 |
| 4 | 11-25 |
| 5 | 26-50 |
| 6 | 50-100 |

Azelaic acid, applied alone or in combination with salicylate, kaolin, or combinations thereof, provided protection from heat, water and light stress that was equivalent to or better than the standard treatments as shown by the percent of the bunches of grapes having a rating of 1 and 2, by yield as measured in kilograms per vine, by average weight of a bunch and by yield as measured in kilograms per hectare. See Table 6, below.

TABLE 6

Summary of the data from the wine grape field trials.

| | | 10-Mar-10 | | | |
|---|---|---|---|---|---|
| Treatment | Rate* | % Bunches Rating 1 + 2 | Yield kg/ vine | Bunch Weight (grams) | Yield kg/ha |
| Untreated | | 70.3 | 2.08 | 56.9 | 5333 |
| Screen | 2.5% fb 1.25% | 97.5 | 3.63 | 96.8 | 9307 |
| Screen Duo | 1.25% fb 0.65% | 98 | 3.5 | 93.5 | 8974 |
| Azeleic acid (CMM2009A) | 8 g/ha | 96.8 | 3.6 | 94.7 | 9230 |
| Screen + Azeleic acid | 2.5% + 8 g/ha fb 1.25% + 8 g/ha | 91.9 | 3.45 | 85.7 | 8846 |
| Screen Duo + Azeleic acid | 1.25% + 8 g/ha fb 0.65% + 8 g/ha | 91.4 | 3.38 | 88.1 | 8666 |
| Azeleic acid + Salicylate | 8 g/ha $10^{-4}$M | 91.7 | 3.5 | 89.5 | 8974 |
| Azeleic acid + Glycine Betaine | 8 g/ha $10^{-4}$M | 85.9 | 3.18 | 85.1 | 8154 |
| Surround | 5.0% fb 2.5% | 93.7 | 3.3 | 83.1 | 8461 |
| Parasol | 2 fb 1 L/100 L | 88.4 | 2.75 | 75.7 | 7051 |
| LSD 0.05 | | 13.56 | 0.49 | 14.9 | 1256 |

*Four applications for all treatments.

Example 7

Sebacic Acid Trial

A tomato pot study was conducted with sebacic acid to determine the activity of sebacic acid in increasing tolerance to abiotic stress. The tomatoes were grown in a standard medium in pots and subjected to the abiotic stresses of high heat, light, and water stress. Growth of the plants was used as a measure of the ability of the sebacic acid to reduce the impact of abiotic stress. Growth measurements were taken 32 days after treatment with sebacic acid

TABLE 7

Summary of the tomato/sebacic acid pot trials.

| Treatment | Growth (mm) |
|---|---|
| Control | 23.2 |
| Sebacic 1 × 10−4M | 25.3 |
| LSD0.05 | 2.07 |

The results show a statistically significant greater growth for the sebacic acid-treated plants compared with the untreated plants (Table 7).

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

That which is claimed is:

1. A method for increasing tolerance to abiotic stress and/or reducing the consequence of abiotic stress in a plant or part thereof, comprising:
contacting said plant or part thereof with a composition comprising an effective amount of sebacic acid (decanedioic acid, HOOC—$(CH_2)_8$—COOH) and/or a salt thereof, wherein the concentration of sebacic acid in the composition is $8\times10^{-4}$M to about $1\times10^{-9}$M, and the plant or plant part is not cucumber or pea, thereby increasing tolerance to abiotic stress and/or reducing the consequence of abiotic stress in said plant and/or plant part thereof.

2. The method of claim 1, wherein the abiotic stress is selected from the group consisting of cold temperature, freezing, chilling, heat or high temperature, drought, salinity, high light intensity, ozone, and any combination thereof.

3. The method of claim 1, wherein the abiotic stress is a combination of abiotic stresses selected from the group consisting of high temperature and high light intensity; high temperature, high light intensity and drought; high temperature and drought; high light intensity and drought; and cold temperature or chilling and high light intensity.

4. The method of claim 1, wherein the consequence of abiotic stress is selected from the group consisting of sunburn damage, flower-abortion, fruit drop, reduced fruit size, reduced cell division, reduced yield, reduced quality of produce due to appearance and texture, and any combination thereof.

5. The method of claim 1, wherein the combination of abiotic stress is high temperature and high light intensity and the consequence of the abiotic stress is sunburn damage.

6. The method of claim 1, wherein the composition further comprises an effective amount of at least one dicarboxylic acid selected from the group consisting of undecanedioic acid (HOOC—$(CH_2)_9$—COOH), pimelic acid (heptanedioic acid, HOOC—$(CH_2)_5$—COOH), suberic acid (octanedioic acid, HOOC—$(CH_2)_6$—COOH), azelaic acid (nonanedioic acid, HOOC—$(CH_2)_7$—COOH), dodecanedioic acid (HOOC—$(CH_2)_{10}$—COOH), brassylic acid (tridecanedioic acid, HOOC—$(CH_22)_{11}$-COOH), thapsic acid (hexadecanedioic acid, HOOC—$(CH_2)_{14}$—COOH), tetradecanedioic acid (HOOC—$(CH_2)_{12}$—COOH), pentadecanedioic acid (HOOC—$(CH_2)_{13}$—COOH), and salts thereof, and any combination thereof.

7. The method of claim 1, wherein the step of contacting is selected from the group consisting of spraying, dusting, sprinkling, scattering, misting, atomizing, broadcasting, soaking, soil injection, soil incorporation, pouring, coating, side dressing, seed treatment, soil treatment, and any combination thereof.

8. The method of claim 1, wherein the composition further comprises an agriculturally acceptable carrier.

9. The method of claim 1, wherein sebacic acid or a salt thereof is applied in combination with one or more active component, wherein said active component is selected from the group consisting of a plant hormone, an amino acid, a nutrient, a micronutrient, a terpene, a pesticide, a fungicide, and any combination thereof.

10. The method of claim 1, wherein the plant is selected from the group consisting of woody, herbaceous, horticultural, agricultural, forestry, nursery, ornamental plant species, plant species useful in the production of biofuels, and any combination thereof.

11. The method of claim 1, wherein the plant is selected from the group consisting of apple, tomato, pear, pepper, green bean, dried bean, squash, honeydew melon, watermelon, cantaloupe, papaya, mango, pineapple, avocado, plum, cherry, peach, apricot, nectarine, grape, strawberry, raspberry, blueberry, cranberry, gooseberry, banana, fig, clementine, kumquat, orange, grapefruit, tangerine, mandarin, lemon, lime, hazelnut, pistachio, walnut, macadamia, almond, pecan, *Litchi*, soybeans, corn, sugar cane, peanuts, cotton, canola, oilseed rape, rapeseed, alfalfa, timothy, tobacco, sugarbeet, potato, carrot, wheat, rice, barley, rye, millet, sorghum, oat, triticale, buckwheat, quinoa, sunflower, turf, lettuce, roses, tulips, violets, basil, oil palm, elm, ash, oak, maple, fir, spruce, cedar, pine, birch, cypress, coffee, miscanthus, arundo, switchgrass, and any combination thereof.

12. The method of claim 1, wherein the composition comprising an effective amount of sebacic acid and/or a salt thereof further comprises additional active compounds selected from the group consisting of a fertilizer, a plant nutrient, a plant micronutrient, an amino acid, a plant hormone, a pesticide, a fungicide, an insecticide, a nematicide, a reflective material, and any combination thereof.

13. The method of claim 1, wherein the reflective material comprises kaolin.

\* \* \* \* \*

UNITED STATES PATENT AND TRADEMARK OFFICE
CERTIFICATE OF CORRECTION

PATENT NO. : 9,648,877 B2  
APPLICATION NO. : 14/467911  
DATED : May 16, 2017  
INVENTOR(S) : Kupatt Page 1 of 1

It is certified that error appears in the above-identified patent and that said Letters Patent is hereby corrected as shown below:

On the Title Page

(71) Applicant: Please correct "Apex, NC" to read -- Raleigh, NC --

(72) Inventor: Please correct "Apex, NC" to read -- Raleigh, NC --

Signed and Sealed this  
Twenty-fourth Day of April, 2018

Andrei Iancu  
*Director of the United States Patent and Trademark Office*